United States Patent [19]

Wu

[11] 4,230,456
[45] Oct. 28, 1980

[54] ELEMENT AND ASSAY FOR ALBUMIN

[75] Inventor: Tai-Wing Wu, Rochester, N.Y.

[73] Assignee: Eastman Kodak Company, Rochester, N.Y.

[21] Appl. No.: 938,122

[22] Filed: Aug. 30, 1978

[51] Int. Cl.³ .................. G01N 33/68; G01N 21/64
[52] U.S. Cl. .................................. 23/230 B; 23/902; 422/56; 422/57
[58] Field of Search ............... 23/230 B, 902; 422/56, 422/57

[56] References Cited

U.S. PATENT DOCUMENTS

| | | | |
|---|---|---|---|
| 3,063,812 | 11/1962 | Collins | 23/230 B |
| 3,485,587 | 12/1969 | Keston | 23/230 B |
| 3,558,278 | 1/1971 | Louderback | 23/230 B |
| 3,672,845 | 6/1972 | Verbeck | 23/253 TP |
| 3,741,876 | 6/1973 | Guilbault | 195/103.5 R |
| 3,873,272 | 3/1975 | Wakefield | 23/230 B |
| 3,992,158 | 11/1976 | Przybylowicz | 23/253 TP |
| 4,000,975 | 1/1977 | Christenbury | 23/230 B |
| 4,018,883 | 4/1977 | Parslow | 424/1 |
| 4,050,898 | 9/1977 | Goffe | 23/253 TP |
| 4,069,016 | 1/1978 | Wu | 23/230 B |
| 4,144,306 | 3/1979 | Figueras | 422/56 |
| 4,153,668 | 5/1979 | Hill | 23/902 X |
| 4,166,093 | 8/1979 | Smith-Lewis | 422/56 |

OTHER PUBLICATIONS

J. J. Betheil, Anal. Chem., 32, 560 (1960).
G. H. Grant et al., "Fundamentals of Clinical Chemistry", 2nd Edition, p. 337, 1976.
D. C. Cannon et al., "Clinical Chemistry", 2nd Edition, pp. 449–451, 1974.
V. H. Rees et al., J. Clin. Path., 7, 336 (1954).
G. M. Edelman et al., "Fluorescent Probes and the Conformation of Proteins", from Accounts of Chemical Research, vol. 1, No. 3, Mar. 1968.
J. Steinhardt et al., "Multiple Equilibria in Proteins", pp. 302–316, Academic Press, New York, 1969.
K. Kono et al., Chem. Phar. Bull., vol. 18, p. 1287, (1970).
Chemical Abstracts, 86: 145960y, (1977).

Primary Examiner—Sidney Marantz
Attorney, Agent, or Firm—Torger N. Dahl

[57] ABSTRACT

Analytical elements and methods for the detection of albumin in liquid samples feature an albumin-active complex comprising a detectable species bound to a carrier. The detectable species has a sufficiently high affinity for albumin that, when contacted with a liquid solution containing albumin, the detectable species separates from the albumin-active complex and becomes bound to albumin to form a complex comprising albumin and detectable species. The presence of albumin can be detected and, if desired, quantified by determining either the reduction of detectable species in the albumin-active complex of the formation of a complex comprising albumin and detectable species.

13 Claims, 1 Drawing Figure

ELEMENT CALIBRATION OF HSA AT pH 7.40 AND 37° C.

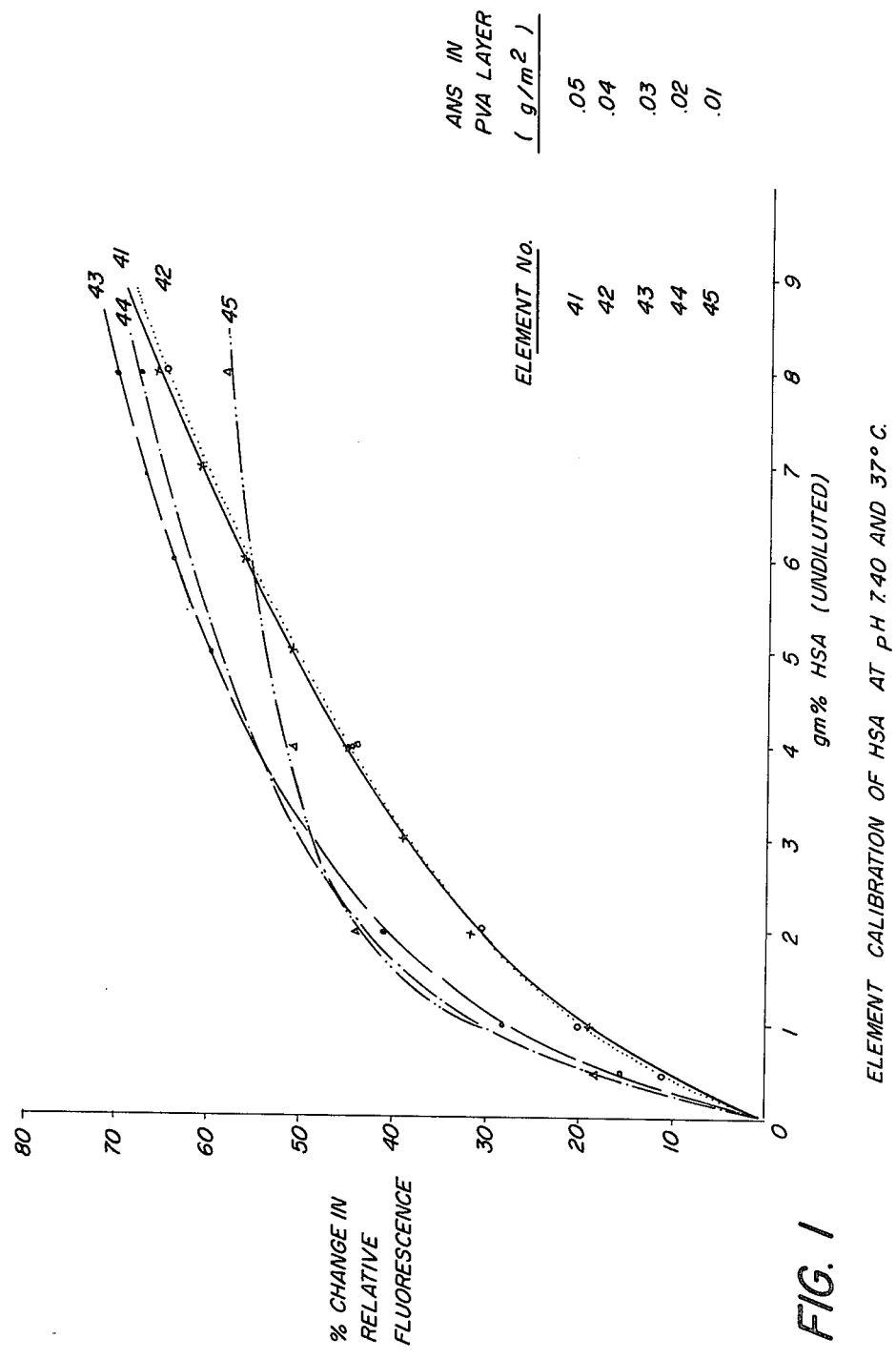

ELEMENT AND ASSAY FOR ALBUMIN

The present invention relates to an assay for albumin and, more particularly, to methods and elements capable of detecting and quantifying albumin in biological fluids and other liquids.

Albumin is the smallest and most abundant of plasma proteins, generally constituting slightly over half of the total protein in the plasma. Albumin has a molecular weight of about 69,000, is synthesized in the liver and has a half-life of four weeks. It has two important roles: (a) regulating the water balance between blood and tissues, and (b) functioning as a transport molecule for various materials which are only slightly soluble in water, such as bilirubin, fatty acids, cortisol, thyroxine, and any number of drugs including sulfonamides and barbiturates.

It is frequently important to determine whether patients have a deficiency of serum albumin. Patients having a deficiency of serum albumin suffer from edema, characterized by an abnormal accumulation of serous fluid. Also, albumin deficiency can interfere with the transport of insoluble materials. Accordingly, there is a need for procedures and materials which can detect the quantify albumin in body fluids.

Resse et al, in *J. Clin. Path.* (1954), 7, 336, show that the amount of albumin in an aqueous dilute sample of serum can be quantified by using the dye-binding capacity of a substance such as 1-anilinonaphthalene-8-sulfonic acid (ANS). In its unbound state, ANS is non-fluorescent in aqueous solution, but fluoresces brightly when adsorbed by plasma albumin. In order to avoid interference by bilirubin, Reese et al employed dilute solutions of blood serum in making their analysis. It would, of course, be highly advantageous to provide an assay for albumin which does not require dilution in order to avoid bilirubin interference.

In one aspect, this invention comprises an analytical element for the detection of albumin in a liquid sample. The element comprises a reagent zone which contains an albumin-active complex comprising a detectable species bound to a carrier. The detectable species has a sufficiently high affinity for albumin that, when contacted with a liquid solution containing albumin, the detectable species separates from the albumin-active complex and becomes bound to albumin to form a complex comprising albumin and detectable species. Albumin can be detected by (a) the presence of detectable species bound to albumin, or (b) a reduction in the amount of detectable species in said albumin-active complex. If desired, a determination can be made of the amount of detectable species bound to albumin, or the amount of reduction of detectable species in the albumin-active complex, to quantify the amount of albumin present in the liquid sample.

In one preferred aspect, the invention comprises an essentially dry multilayer element for quantifying the amount of albumin in an aqueous liquid sample. The element of this aspect of the invention comprises an isotropically porous spreading layer superposed over a reagent layer carried on a radiation-transmissive support, the spreading and reagent layers being in fluid contact with one another under conditions of use. The reagent layer comprises an albumin-active complex comprising a detectable species bound to a carrier, the detectable species having a sufficiently high affinity for albumin that, when contacted with an aqueous liquid solution containing albumin, the detectable species selectively separates from the albumin-active complex and becomes bound to albumin. The amount of albumin present in the liquid sample can be quantified by determining (a) the amount of detectable species bound to albumin, or (b) the reduction in the amount of albumin-active complex.

Another aspect of this invention provides an improvement in the method for detecting albumin in a liquid sample which comprises contacting the liquid sample with a detectable species, forming a complex between detectable species and any albumin present in the liquid sample, and detecting, directly or indirectly, the formation of the complex. The improvement in accordance with this aspect of the invention features, as the detectable species which is contacted with the liquid sample, an albumin-active complex comprising detectable species and a carrier; the detectable species having a sufficiently high affinity for albumin that, when the albumin-active complex is contacted with a liquid sample comprising albumin, the detectable species separates from the albumin-active complex and forms a complex with albumin.

Another preferred method for quantifying the amount of albumin in a liquid sample comprises:

A. contacting the liquid sample with an albumin-active complex comprising a detectable species bound to a carrier;

B. separating the detectable species from the carrier of the albumin-active complex and binding the detectable species to albumin; and C. determining the amount of detectable species which separates from the albumin-active complex and becomes bound to albumin.

The albumin-active complex employed in the practice of this invention comprises a detectable species bound to a carrier. The albumin-active complex is chosen so that, when contacted with a liquid solution containing albumin, the detectable species separates from the albumin-active complex and becomes bound to albumin. In at least one state, that is, either when bound to the carrier of the albumin-active complex or when bound to albumin, the detectable species exhibits identifiable color or fluorescence. In a preferred aspect of the invention, the albumin-active complex is fluorescent; the fluorescence of the complex is reduced selectively (i.e., in proportion to the amount of albumin) when contacted with an aqueous solution containing albumin.

The present invention employs a "competitive binding" feature, which is more specific, and less prone to interference from other materials in serum (or other samples containing albumin).

In the practice of this invention, it appears that the albumin normally does not penetrate into the reagent layer; rather, it is believed that when the liquid sample containing albumin is applied to the spreading layer, the detectable species migrates from the reagent layer and binds to albumin in the spreading layer or the interface between the reagent layer and spreading layer.

BRIEF DESCRIPTION OF THE DRAWING

The accompanying drawing plots of the percent change in fluorescence against the amount of albumin in various liquid samples, using test elements containing differing amounts of detectable species in accordance with the invention.

Suitable detectable species include fluorescent probes, such as those described in and referred to in

*Multiple Equilibria Proteins* by Steinhardt and Reynolds (1969), Academic Press, pages 302 through 314. Particularly good results are obtained with 1-anilinonaphthalene-8-sulfonic acid (ANS) and other anionic sulfonated or indicator dyes, such as 2,6-TNS (2-p-toluidinylnaphthalene-6-sulfonate), 1-4-ANS (1-anilinonaphthalene-4-sulfonate) and AcR (an arsenic organic compound) [5-(4'-arsonoanilino)-2-chloro-7-methoxyacridine]. The carrier in the albumin-active complex can comprise polyvinyl alcohol, gelatin, styrene/N-vinylbenzyl-N,N-dimethylbenzyl ammonium chloride/divinylbenzene terpolymers, styrene/ammonium chloride and N-x-vinylbenzyl-N,N,N-trihexyl copolymers, Cholestyramine (trademark of Johnson and Johnson Company) and known mordants (preferably polymeric), e.g., a bis(methacryloyloxyethyl)malonate polymer, poly(styreneco-N-vinylbenzyl-N,N-dimethylbenzyl ammonium chloride-codivinylbenzene, or those basic polymeric mordants, e.g., described in U.S. Pat. Nos. 2,882,156 and 3,709,690.

One particularly useful complex, which is preferred in accordance with the practice of this invention, comprises a fluorescent albumin-active complex comprising ANS and polyvinyl alcohol. Also, in a preferred aspect of this invention, the complex of polyvinyl alcohol and ANS are the essential constituents of the reagent layer. When albumin is quantified by measuring reagent formation of the complex of albumin and detectable species, it is desirable to employ a transparent spreading layer and an opaque reagent layer. Any suitable opacifying agent can be used, such as $TiO_2$.

The elements of this invention preferably include a spreading layer. The spreading layer is a layer than can accept a liquid sample, whether applied directly to the spreading layer or provided to it from a layer or layers in fluid contact with the spreading layer, and within which the solvent or dispersion medium of the sample and albumin is distributed such that a uniform apparent concentration of albumin is provided at the surface of the spreading layer facing the reagent layer of the element.

Useful spreading layers are desirably isotropically porous layers. Isotropic porosity connotes porosity in all directions within the spreading layer; a further description of this term appears in U.S. Pat. No. 3,992,158.

Particulate material can be used to form isotropically porpous layers, wherein the isotropic porosity is created by interconnected spaces between the particles. Various types of particulate matter, all desirably chemically inert to sample components under analysis, are useful. Pigments, such as titanium dioxide, barium sulfate, zinc oxide, lead oxide, etc., are desirable, to make the layer opaque, so that it can function as a reflecting layer. Other desirable particles are diatomaceous earth and microcrystalline colloidal materials derived from natural or synthetic polymers, e.g., microcrystalline cellulose.

Preferably, the spreading layer is prepared using isotropically porous polymer compositions, as described in U.S. Pat. No. 3,992,158, the disclosure of which is incorporated herein by reference. It is possible to prepare such polymer compositions using techniques useful in forming blushed polymers, for example, as described in U.S. Pat. No. 3,555,129. Other techniques useful in preparing isotropically porous polymer compositions include those relating to the use of gas or other swellable constituents to create pores, as described in U.S. Pat. Nos. 2,960,728 and 2,946,095; or to the use within the polymer phase of a dissolvable solid that is dissolved to provide pores, for example, as discussed in U.S. Pat. No. 3,816,575.

Useful spreading layers can be prepared using a variety of components as described in U.S. Pat. No. 3,992,158. Spreading layers can be prepared by coating from solution or dispersion. The materials useful for inclusion in any spreading layer will usually include predominantly materials which are resistant to water; i.e., they are substantially insoluble in and nonswellable upon contact with water or other liquid under analysis. Swelling of about 10 to 14 percent of the layer's dry thickness may be normal. The thickness of the spreading layer is variable and will depend in part on the intended sample volume, which for convenience and cleanliness the spreading layer should be able to absorb, and on the layer's void volume, which also affects the amount of sample that can be absorbed into the layer. Spreading layers of from about 50 microns to about 300 microns dry thickness have been particularly useful. However, wider variations in thickness are acceptable and may be desirable for particular elements.

The present analytical elements can be self-supporting or carried on a support. Useful support materials include a variety of polymeric materials, such as cellulose acetate, poly(ethylene terephthalate), polycarbonates and polyvinyl compounds, such as polystyrenes, etc. A support of choice for any particular element will be compatible with the intended mode of albumin detection. Preferred supports include radiation-transmissive support materials that transmit electromagnetic radiation of a wavelength or wavelengths within the region between about 200 nm and about 900 nm, as well as radiation due to radioactivity. For fluorimetric detection of analytical results through the support, it is desirable for the support to transmit over a somewhat wider band than is necessary for nonfluorescence measurements or, alternatively, to transmit at the absorption and emission spectra of the fluorescent materials used for detection. It may also be desirable to have a support that transmits one or more narrow wavelength bands and is opaque to adjacent wavelength bands. This could be accomplished, for example, by impregnating or coating the support with one or more colorants having suitable absorption characteristics. When an element includes a support, the reagent layer will usually be interposed between the support and the spreading layer (if present), which often is the outermost layer in the element.

As can be appreciated, a variety of different elements, depending on the method of analysis, can be prepared in accordance with the present invention. Elements can be configured in a variety of forms, including elongated tapes of any desired width, sheets or smaller chips.

The prepared elements are placed in use by applying to the element a sample of liquid under analysis. Typically, an element will be formed such that an applied sample will contact a spreading layer, if present, prior to contacting the reagent layer and will first contact such spreading layer at its surface furthest removed from such reagent layer. Because analytical accuracy of the present elements is not substantially diminished by variations in the volume of applied samples, especially when a spreading layer is present in the element, sample application by hand or machine is acceptable. For reasons of convenience in detecting an analytical result, however, reasonable consistency in sample volume may be desirable.

In a typical analytical procedure using the present elements, which could be manual or automated, the element is taken from a supply roll, chip packet or other source and positioned to receive a free drop, contact spot or other form of liquid sample, such as from an appropriate dispenser. After sample application, and desirably after the liquid sample has been taken up by a spreading layer, if present, the element is exposed to any conditioning, such as incubation, heating, or the like, that may be desirable to quicken or otherwise facilitate obtaining any test result. If an automated procedure is used, it can also be desirable to have any spreading layer accomplish its function within several seconds, but allowing sufficient time to provide metering.

After the analytical result is obtained as a detectable change, it is measured, usually by passing the element through a zone in which suitable apparatus for reflection, transmission or fluorescence spectrophotometry is provided. Such apparatus would serve to direct a beam of energy, such as light, through the support and the reagent layer. The light would then be reflected, such as from a radiation-blocking layer in the element, back to a detecting means or would pass through the element to a detector, in the case of transmission detection. In a preferred mode, the analytical result is detected in a region of the element (e.g., the reagent layer) totally within the region in which such result is produced. Use of reflection spectrophotometry can be advantageous in some situations as it can effectively avoid interference from residues, such as globulin or blood cells, which may have been left on or in the layers of the element.

Conventional techniques of fluorescence spectrophotometry can also be employed if the detectable species exhibits an increase or decrease in fluorescence, as compared with its fluorescence when bound to the carrier of the albumin-active complex. Detection would be accomplished using energy which excites the fluorescent species and a detector which senses its fluorescent emission. Generally, electromagnetic radiation in the range of from about 200 to about 900 nm has been found useful for such measurements, although it is possible to use any radiation to which the element is permeable and which is capable of quantifying the change in detectable species in the reagent layer, or the formation of a complex between albumin and detectable species. Various known calibration techniques can be used to provide calibration curves for the analysis.

The invention can be carried out over a wide temperature range, preferably within about 30° to 40° C. The invention is operable over a wide pH range, pH's from 6 to 8.5 giving good results. The useful concentration of detectable species in the elements of the invention will depend on the particular element and material selected; with the highly useful fluorescent probe ANS, particularly good results are achieved in elements in accordance with the invention containing from about 0.01 to about 0.05 grams ANS per square meter or more; particularly good results are obtained with about 0.04 to 0.05 grams per square meter ANS. The carrier for the detectable species is present in amounts of 0.5 to 3, and preferably about 1.5 to 2.5 grams per square meter.

The following examples are presented as a further illustration of the invention. In these examples, the following materials and abbreviations for these materials are employed:

Human serum albumin (HSA)—Fraction V powders, fatty acid-free and γ-globulin freeze-dried, purchased from Miles Laboratories, Inc.

8-anilinonaphthalene-1-sulfonate (ANS)—fluorescent probe purchased as the magnesium salt from Eastman Organic Chemicals. This material has the structure:

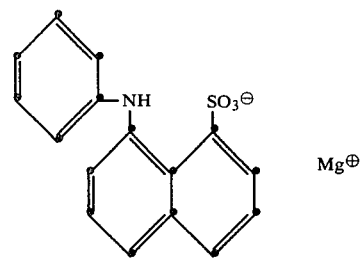

Element Formulation

Elements referred to as Elements 41 through 45 in the following formulations were prepared and were used in the examples.

| Spreading Layer* | TiO$_2$ | | | 56 g/m$^2$ | |
|---|---|---|---|---|---|
| | cellulose acetate | | | 7.9 g/m$^2$ | |
| Subbing Layer | poly-n-isopropylacrylamide | | | 0.4 g/m$^2$ | |
| Reagent Layer | | | ANS | | |
| | .01 g/m$^2$ | .02 g/m$^2$ | .03 g/m$^2$ | .04 g/m$^2$ | .05 g/m$^2$ |
| | Element 45 | Element 44 | Element 43 | Element 42 | Element 41 |
| | | | Poly(vinyl alcohol) (PVA) 1.7 g/m$^2$ | | |
| Support | | | cellulose acetate support | | |

*prepared as in Example 1 of U.S. Pat. No. 3,992,158

Assay Procedure

The assay procedure used was as follows:

Albumin standards containing 0 to 8 g percent of freshly prepared human serum albumin (HSA) in 0.05 M phosphate buffer at pH 7.40 and 37° C. were spotted, in 10 μl aliquots, onto the spreading layer of the elements and the decrease in fluorescence (ΔF, expressed as percent equals $$\frac{F(mV) \text{ no albumin} - F(mV) \text{ with albumin}}{F(mV) \text{ no albumin}} \times 100)$$

was monitored at an excitation frequency of 340 to 360 nm and an emission frequency of 440 to 600 nm using a spectrofluorometer equipped for fluorescence measurements. A correlation between the change in fluorescence, ΔF percent, and the concentration of HSA is seen in FIG. 1. Usually, the ΔF percent became invariant or leveled off in less than 2 to 3 minutes.

EXAMPLE 1: Calibration of HSA at pH 7.4 and 37° C.

Elements 41 through 45 were tested according to the assay procedure described above. FIG. 1 shows that all five elements responded to albumin concentrations. Elements 41 and 42, containing 0.05 and 0.04 g/m$^2$ of ANS, respectively, gave the best discrimination among all the albumin levels tested. However, it was observed that Element 41 (0.04 g/m$^2$) gave the best reproducibility in results and was the preferred formulation of those tested.

EXAMPLE 2: Effect of pH on Element Response

To observe the effect of pH variation on the element of the present invention, three levels of albumin standards (0, 1.0 g percent and 4.0 g percent) were adjusted to five different pH values (with sodium phosphate buffer), as shown in Table 1. These solutions were then spotted onto Element No. 41 and evaluated as described above. As seen in Table 1, this variation in pH (range 6.0 to 8.5), has no appreciable effect on element response. Normal serum pH is between 7.34 to 7.45. Proper buffering of the element will insure that the reaction occurs within a narrow pH range.

EXAMPLE 4: Effect of γ-globulin Level on Element (at pH 7.4 and 37° C.)

A. In the Absence of HSA

Aqueous solutions containing varying levels of γ-globulin (between 0 to 3.0 g percent) were spotted onto Element No. 41. None of the solutions elicited more than a 3 to 6 percent change in F. Attempts to test higher globulin levels were prohibited by the insolubility of this protein at pH 7.0 to 7.4.

B. In the Presence of HSA

The same element was spotted with solutions containing both albumin and γ-globulin in ratios as shown in Table 3. As can be seen in this table, the element response appeared to be relatively insensitive to the γ-globulins. This observation was consistent with that in Part A.

TABLE 1

Effect of pH Variation on Relative Fluorescence (mV) and % Change in Fluorescence (ΔF%) at 37° C.

| pH: | 6.0 | | 7.0 | | 7.4 | | 8.0 | | 8.5 | |
| --- | --- | --- | --- | --- | --- | --- | --- | --- | --- | --- |
| g% HSA | *F(mV) | ΔF% | F(mV) | ΔF% | F(mV) | ΔF% | F(mV) | ΔF% | F(mV) | ΔF% |
| 0 | 1810 | 0 | 1800 | 0 | 1800 | 0 | 1793 | 0 | 1795 | 0 |
| 1 | 1386.5 | 23.4 | 1371.6 | 23.8 | 1364.4 | 24.2 | 1350.7 | 24.5 | 1351.6 | 24.7 |
| 4 | 999.1 | 44.8 | 990 | 45.0 | 986.4 | 45.2 | 977.2 | 45.5 | 994.4 | 44.6 |

*F(mV) represents the fluorescence registered at 2 minutes after wetting the element. The dry element background in all runs was preset at or around 2000 mV. Thus, the F at 0 gm percent albumin would correspond to the wet background which, as shown, appears fairly constant over the pH range tested.

EXAMPLE 3: Effect of Temperature at pH 7.4

The same albumin standards as used in Example 2 at pH 7.4 were spotted onto Element No. 41 and tested at various temperatures, as shown in Table 2. Over the temperature range examined (30° to 40° C.), overall fluorescent levels decreased somewhat with increasing temperatures, while the ΔF percent induced by the presence of albumin increased slightly. The magnitude of these effects, however, appeared relatively small.

TABLE 2

Effect of Temperature on Relative Fluorescence (mV) and % Change in Fluorescence (mV)

| | Temperature °C. | | | | | |
| --- | --- | --- | --- | --- | --- | --- |
| HSA | 30° | | 37° | | 40° | |
| g% | F(mV) | % ΔmV | F(mV) | % ΔmV | F(mV) | % ΔmV |
| 0 | 1990 | 0 | 1820 | 0 | 1759 | 0 |
| 4 | 1110 | 44.2 (39) | 997.4 | 45.2 | 914.7 | 48 (49.7) |
| 8 | 742.3 | 62.7 (59.2) | 604.24 | 66.8 | 545.3 | 69 (70) |

All assays were performed at pH 7.40. Numbers within parentheses are calculated on the basis of the F with 0 percent albumin at 37° C. as the arbitrary wet background. Otherwise, percent mV was calculated on the basis of the wet background at each set of temperatures tested.

TABLE 3

Effect of Varying Albumin/γ-Globulin Ratios on Relative F(mV) and % Change in F

| | Albumin/Globulin or A/G Ratio | | | | | |
| --- | --- | --- | --- | --- | --- | --- |
| | 1.0 | | 1.33 | | 1.8 | |
| Actual HSA Level, g% | F(mV) | % ΔmV | F(mV) | % ΔmV | F(mV) | % ΔmV |
| 0 | 1810 | 0 | 1799 | 0 | 1804 | 0 |
| 3.5 | 1026.3 | 43.3 | 1005.6 | 44.1 | 977.77 | 45.8 |
| 4.0 | 962.9 | 46.8 | 924.7 | 48.6 | 952.5 | 47.2 |
| 4.5 | 924.9 | 48.9 | 913.9 | 49.2 | 905.6 | 49.8 |

All test media in both A and B were adjusted to pH 7.4 in 0.05 M sodium phosphate buffer and studied at 37° C. Again, the mV registered at 0 percent albumin served as the "wet" background, and was used to calculate percent ΔF.

EXAMPLE 5: Effect of Varying NaCl (at pH 7.4 and 37° C.)

In order to test element response to salt concentrations in sera, various concentrations ranging from 0 to 150 mM NaCl were added to standard solutions containing 0, 1.0 and 4 g percent albumin. As shown in Table 4, this large variation in salt concentration produced remarkably little change in the calibration of albumin.

TABLE 4

Effect of Salt Concentration on Relative Fluorescence (mV) and % Change of Fluorescence

| | NaCl (mM) | | | | | | | |
| --- | --- | --- | --- | --- | --- | --- | --- | --- |
| | 0 | | 50 | | 100 | | 150 | |
| HSA (g%) | mV | % ΔmV | mV | % ΔmV | mV | % ΔmV | mV | % ΔmV |
| 0 | 1816 | 0 | 1805 | 0 | 1793 | 0 | 1788 | 1.5 |
| 1 | 1366.5 | 24.75 | 1376.3 | 23.75 (24.2)* | 1372 | 23.7 (24.45)* | 1334 | 25.4 (27)* |
| 4 | 904.4 | 50.2 | 969.3 | 46.3 | 868.4 | 51.7 | 924.4 | 48.3 |

TABLE 4-continued
Effect of Salt Concentration on Relative Fluorescence (mV) and % Change of Fluorescence

| HSA (g%) | NaCl (mM) | | | | | | | |
|---|---|---|---|---|---|---|---|---|
| | 0 | | 50 | | 100 | | 150 | |
| | mV | % ΔmV | mV | % ΔmV | mV | % ΔmV | mV | % ΔmV |
| | | | (46.62)* | | (52)* | | (49)* | |

*The determinations were conducted at 37° C. and at pH 7.4, as described in Tables 1 through 3. Numbers within parentheses are the percent change in F (pecent ΔmV) based on the "0 albumin-0 NaCl" solution (which actually has 0.05 M sodium phosphate buffer, pH 7.4), as given in the top left column of the table. Otherwise, the percent ΔmV are calculated on the basis of the 0 albumin solution at each indicated NaCl level.

It may be noted that the normal levels of serum chloride ions and sodium ions are 98 to 108 mM and 135 to 148 mM, respectively. The above data imply that the element of the present invention is tolerant to considerable alterations in salt concentrations in serum.

Solution detection and quantization of albumin is possible in accordance with the present invention. An ANS-PVA complex, when excited at 380 nm, emits at 520 nm. An ANS-Albumin complex, when excited at 386 nm, emits at 475 nm, and with an intensity about 1,000 times stronger than the ANS-PVA complex. Because ANS has a much higher affinity for albumin than PVA, solution detection and quantization is feasible.

Although the invention has been described in considerable detail with particular reference to certain preferred embodiments thereof, variations and modifications can be effected within the spirit and scope of the invention.

I claim:

1. An analytical element for the detection of albumin in a liquid sample, said element comprising a reagent zone which contains an albumin-active complex comprising a detectable species bound to a carrier;

said detectable species having a sufficiently high affinity for albumin that, when contacted with a liquid solution containing albumin, said detectable species separates from said albumin-active complex and becomes bound to albumin to form a complex comprising albumin and detectable species;

whereby albumin can be detected by (a) the presence of detectable species bound to albumin, or (b) a reduction in the amount of detectable species in said albumin-active complex.

2. An analytical element for quantifying the amount of albumin in a liquid sample, said element comprising an initially dry reagent zone which contains an albumin-active complex comprising a detectable species bound to a carrier;

said detectable species having a sufficiently high affinity for albumin that, when contacted with a liquid solution containing albumin, said detectable species selectively separates from said albumin-active complex and becomes bound to albumin to form a complex comprising albumin and detectable species;

wherein the amount of albumin present in said liquid sample can be quantified by determining the amount of detectable species which separates from said albumin-active complex and becomes bound to albumin.

3. An analytical element for quantifying the amount of albumin in a liquid sample, said element comprising a radiation-transmissive support having thereon an isotropically porous, opaque spreading layer and a reagent layer between said support and said spreading layer, said reagent layer being in fluid contact with said spreading layer under conditions of use;

said reagent layer comprising a colored or fluorescent albumin-active complex comprising a detectable species bound to a carrier;

said detectable species having a sufficiently high affinity for albumin that, when in fluid contact with a liquid solution containing albumin, said detectable species selectively separates from said albumin-active complex and becomes bound to albumin;

whereby the amount of albumin present in said liquid sample can be quantified by determining the reduction in color or fluorescence of said albumin-active complex.

4. The element of claim 3 wherein said albumin-active complex is a fluorescent complex comprising a fluorescent probe and a polymer.

5. The element of claim 3 wherein said albumin-active complex comprises polyvinyl alcohol and 8-anilinonaphthalene-1-sulfonate.

6. In a method for the detection of albumin in a liquid sample, said method comprising contacting said liquid sample with a detectable species, forming a complex between said detectable species and any albumin present in said liquid sample, and detecting, directly or indirectly, the formation of said complex; the improvement wherein:

said detectable species which is contacted with said liquid sample is in the form of an albumin-active complex comprising said detectable species and a carrier; and, said detectable species has a sufficiently high affinity for albumin that, when said albumin-active complex is contacted with a liquid sample comprising albumin, said detectable species separates from said carrier and forms a complex with albumin.

7. In a method for measuring the amount of albumin in a liquid sample, said method comprising contacting said liquid sample with a detectable species, forming a complex between said detectable species and albumin, and quantifying the amount of albumin in the sample by detecting, directly or indirectly, the amount of said complex formed; the improvement wherein:

said detectable species which is contacted with said liquid is in the form of an albumin-active complex comprising said detectable species and a carrier; and, said detectable species has a sufficiently high affinity for albumin that, when said albumin-active complex is contacted with a liquid sample comprising albumin, said detectable species separates from said carrier and forms a complex with albumin.

8. The method of claim 7 wherein said albumin-active complex is a fluorescent complex comprising a fluorescent probe and a polymer.

9. The method of claim 7 wherein said albumin-active complex comprises polyvinyl alcohol and 8-anilinonaphthalene-1-sulfonate.

10. A method for quantifying the amount of albumin in a liquid sample, said method comprising:
  (a) placing in fluid contact:
    (i) said liquid sample, and
    (ii) an albumin-active complex comprising a detectable species bound to a carrier;
      said detectable species having a sufficiently high affinity for albumin that, when contacted with a liquid solution containing albumin, said detectable species separates from said albumin-active complex and becomes bound to albumin, the amount of detectable species which separates from said albumin-active complex being indicative of the amount of albumin present in said liquid sample;
      whereby said detectable species selectively separates from said carrier and becomes bound to albumin in said liquid sample; and
  (b) selectively detecting the amount of detectable species separated from said albumin-active complex.

11. A method for quantifying the amount of albumin in a liquid sample, said method comprising:
  (a) contacting said liquid sample with an albumin-active complex comprising a detectable species bound to a carrier;
  (b) separating said detectable species from the carrier of said albumin-active complex, and binding said detectable species of albumin; and
  (c) determining the amount of detectable species which separates from said albumin-active complex and becomes bound to albumin.

12. The method of claim 11 wherein said albumin-active complex is a fluorescent complex comprising a fluorescent probe and a polymer.

13. The method of claim 11 wherein said albumin-active complex comprises polyvinyl alcohol and 8-anilinonaphthalene-1-sulfonate.

* * * * *